US00PP12580P2

(12) United States Plant Patent
Hanes

(10) Patent No.: US PP12,580 P2
(45) Date of Patent: Apr. 23, 2002

(54) GERANIUM PLANT NAMED 'FREE BURGUNDY'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/802,865

(22) Filed: Mar. 12, 2001

(51) Int. Cl.[7] ..... A01H 5/00
(52) U.S. Cl. ..... Plt./332
(58) Field of Search ..... Plt./332

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

A geranium cultivar particularly distinguished by green foliage, burgundy flower color, and double flowers on large umbels, fast rooting and exhibits vigorous growth.

1 Drawing Sheet

GENUS AND SPECIES

*Pelargonium peltatum*

VARIETY DENOMINATION

'Free Burgundy'

BACKGROUND OF THE NEW PLANT

Figure 1:
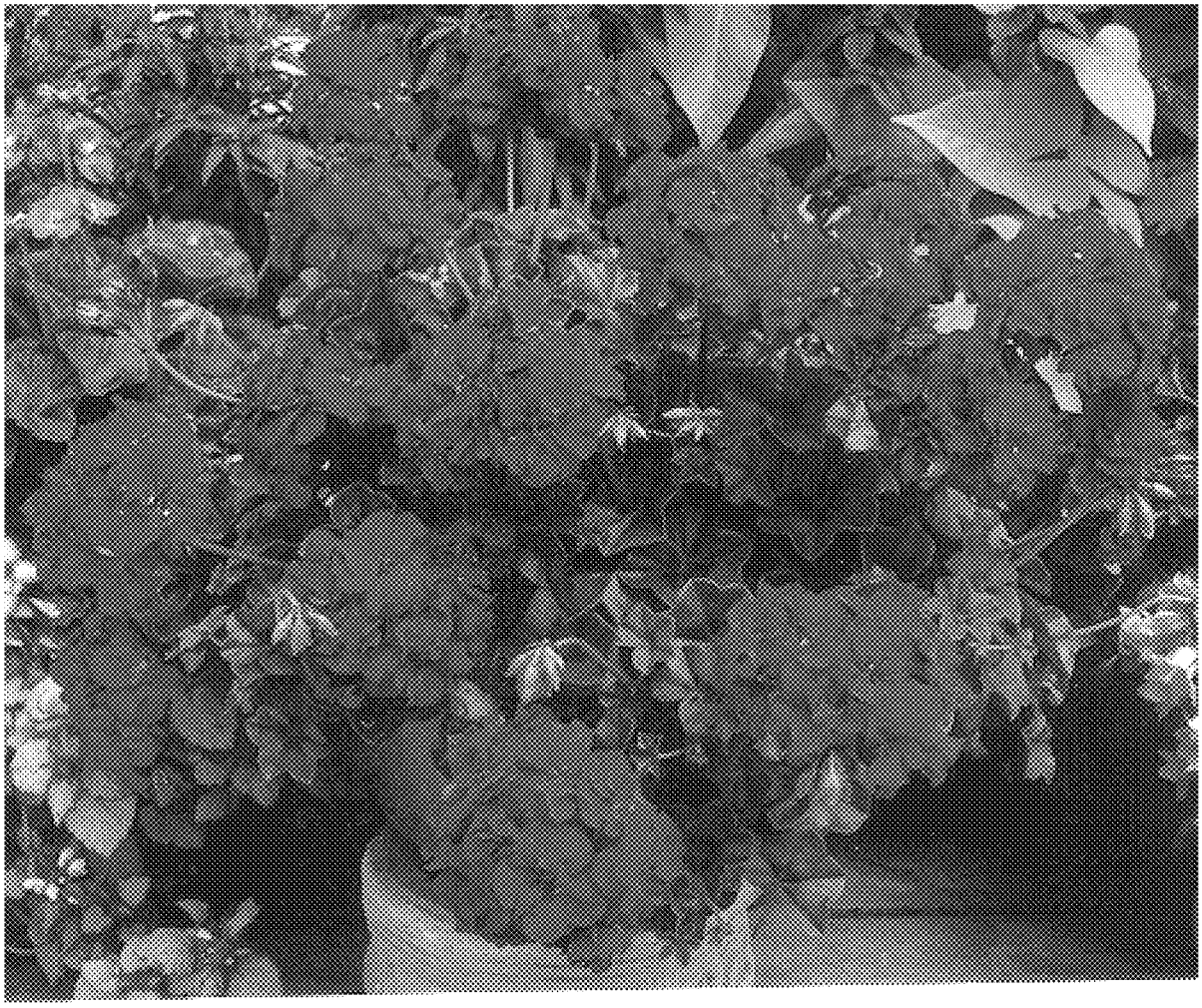

The present invention comprises a new and distinct cultivar of geranium, botanically known as *Pelargonium peltatum* Bailey, and hereinafter referred to by the cultivar name 'Free Burgundy'. The new cultivar is propagated from a seedling resulting from the cross of 7246-1, seed parent, a bright blue-rose and single flowered, unnamed and unpatented proprietary line and 5638-1, pollen parent, a blue-rose flowered, unnamed and unpatented proprietary line.

'Free Burgundy' is a product of a planned breeding program intended to create new geranium cultivars with burgundy colored flowers, double flower form, dark green foliage, vigorous growth and superior cutting productivity.

The new cultivar was created in 1996 in Gilroy, Calif. and has been repeatedly asexually reproduced by cuttings in Gilroy, Calif. and Guatemala over a three year period. It has also been trialed at Gilroy, Calif. and Andijk, The Netherlands. It has been found to retain its distinctive characteristics through successive propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit.

DESCRIPTION OF THE NEW CULTIVAR

The following detailed descriptions set forth the distinctive characteristics of 'Free Burgundy'. The data which defines these characteristics were collected from asexual reproductions carried out in Gilroy, Calif. The plant history was taken on five month old plants grown in 8 inch pots, blossomed under natural light in a greenhouse and color readings were taken in the greenhouse in Gilroy, Calif. Color references are primarily to The R.H.S. Colour Chart of The Royal Horticultural Society of London (R.H.S.).

DETAILED BOTANICAL DESCRIPTION

Classification:
*Botanical.*—*Pelargonium peltatum.*
*Commercial.*—Ivy Geranium.
Form: Upright, spreading.
Height: From soil level to top of plant (excluding blooms) — 16–17 cm; from soil level to top of umbels — 24 cm.
Width: 50–52 cm; if lateral branches are outstretched the width is 75 cm.
Time to produce a finished flowering plant: 13 weeks.
Outdoor plant performance: Good weather tolerance, strong growth.
Time to initiate roots: 8–10 days.
Time to develop roots: 26–28 days.
Root description: White, slightly pubescent, fibrous yet coarse.

The Leaves

Length: 4.5–6.0 cm.
Width: 5.5–6.0 cm depending on age.
Apex description: Cuspidate.
Base description: Cordate, two bottom lobes have acute/cuspidate apice.
Shape: Reniform, five lobes with cuspidate apice.
Margin: Entire, ciliate.
Texture: Very lightly pubescent, somewhat succulent; more pubescent on lower surface along ribs.
Ribs and veins: Palmate, 2.3–2.7 cm long.
Color: Upper side — Yellow-green RHS 146A with a darker zone of 0.5 to 1 cm in width in the center of the leaf that is brown RHS 166A; Under side — Yellow-green RHS 146B; Ribs — Yellow-green RHS 146C; Veins — Yellow-green RHS 146C.
Petiole length: 5.5 . 6.5 cm depending on age of the leaf.
Petiole diameter: 1.7–2.0 mm.
Petiole color: Yellow-green RHS 146C.
Lateral branch length: 20.0–30.0 cm.
Internode length: 1.5–1.8 cm.
Lateral branch color: Yellow-green RHS 146C.

The Bud

Diameter: 6.0 mm.
Length: 1.2 cm.
Shape: Elliptic.
Color when sepals first divide: Red-purple RHS 59B.
Number of sepals: 5 broadly acicular shaped.
Length of sepals: 1.3–1.5 cm.
Width of sepals: 4.0 mm.
Apex description: Cuspidate.
Base description: Truncate.
Sepal color in an open flower: Upper and lower surfaces are yellow-green RHS 144A.

The Flower

Size: Approximately 4.0–4.5 cm in diameter.
Form: Polypetalous, double petaled.
Petals/petaloids: 15 imbricate petals, 2–3 petaloids; Shape: spatulate.
Apex shape: obtuse.
Base shape: attenuate.
Margin: Entire.
Upper petal/petaloid color: Upper petal surface — Burgundy RHS 60A; Petal under surface — burgundy RHS 61C. Petaloid color: Upper surface is burgundy RHS 60A and lower surface — burgundy RHS 60A.
Lower petal/petaloid color: Upper surface petal color is burgundy RHS 60A; underside of petals is burgundy RHS 61C. Upper surface petaloid color is burgundy RHS 60A; and underside is burgundy RHS 60A.
Color change with age: Darkens to red-purple RHS 59A especially along petal margins.
Pedicel length: Approximately 2.5–3.2 cm.
Pedicel color: Yellow-green RHS 144A.
Flower persistence: An open flower will hold its petals until the flower begins to dehisce, or approximately 7–10 days.

The Inflorescence

Type: An umbel composed of approximately 7 flowers.
Diameter: 7.5–9.0 cm.
Depth: 5.0–6.0 cm.
Peduncle length: 11.5–14.0 cm.
Peduncle color: Yellow-green RHS 146A.

The Reproductive Organs

Anthers: 4–5.
Anther color: Red-purple RHS 60A prior to anthesis.
Filament color: Base is white RHS 155A; apex is pink RHS 62B.
Pollen amount and color: Scarce, orange RHS 25A.
Pistil: 1 with a length of 11 mm.
Stigma: 5 linear lobes with a color of purple RHS 71A.
Style: 3.0 mm in length with a color of pink RHS 68D.
Ovary: At anthesis, densely pubescent with white hairs, oblong, green drying to a light brown at maturity.
Seed number: Maximum of 5 per spike.
Seed length: 4–5 mm.
Seed width: 1.0–1.5 mm.
Seed color: Grey-orange RHS 177B that may darken with age.

Disease and Insect Resistance

No susceptibility to diseases or insects noted to date.

Comparison with Known Cultivars

When the instant plant is compared to the parental cultivar 7246-1, 'Free Burgundy' has a darker, redder flower color and the flowers are more double than 7246-1. When compared to 5638-1, 'Free Burgundy' has a darker red flower color and a more branched growth than 5638-1.

I claim:

1. A new and distinct cultivar of geranium plant as shown and described herein.

* * * * *